United States Patent [19]

Pennella

[11] 4,287,378

[45] Sep. 1, 1981

[54] CONVERSION OF OLEFINIC COMPOUNDS

[75] Inventor: Filippo Pennella, Bartlesville, Okla.

[73] Assignee: Phillips Petroleum Company, Bartlesville, Okla.

[21] Appl. No.: 120,223

[22] Filed: Feb. 11, 1980

Related U.S. Application Data

[63] Continuation of Ser. No. 954,723, Oct. 25, 1978, abandoned.

[51] Int. Cl.$^3$ ................................................ C07C 6/00
[52] U.S. Cl. .................................... 585/643; 585/645; 585/646; 585/664; 585/670; 585/671; 204/158 R; 204/162 R
[58] Field of Search ............... 585/500, 643, 645, 646, 585/664, 670, 671; 204/162, 158 R

[56] References Cited

U.S. PATENT DOCUMENTS

| | | | |
|---|---|---|---|
| 3,158,559 | 11/1964 | Caffrey | 585/664 |
| 3,574,076 | 4/1971 | Kirsch | 204/162 |
| 4,060,468 | 11/1977 | Castner | 585/643 |

*Primary Examiner*—Curtis R. Davis

[57] ABSTRACT

A process for the conversion of at least one olefinic organic compound by disproportionation, proportionation, and/or isomerization, in which an olefin conversion catalyst is exposed to electromagnetic radiation prior to and/or during contact of the organic compound with the catalyst. The catalyst may also be pretreated with ethylene, propylene and/or butene during exposure to radiation or the olefinic compound may be pretreated by contact with magnesium oxide while exposing the magnesium oxide to radiation.

45 Claims, 4 Drawing Figures

CONVERSION OF OLEFINIC COMPOUNDS

This application is a continuing application of co-pending application Ser. No. 954,723, filed Oct. 25, 1978, now abandoned.

This invention relates to a process for the conversion of at least one olefinic organic compound. In one aspect, the present invention relates to a process for converting at least one olefinic organic compound to olefinic organic compounds having both higher and lower molecular weights. In another aspect, the present invention relates to a process for converting a mixture of high molecular weight and low molecular weight olefinic organic compounds to olefinic organic compounds of intermediate molecular weight. In yet another aspect, the present invention relates to a process for isomerizing at least one olefinic organic compound.

BACKGROUND OF THE INVENTION

Processes for the conversion of olefinic organic compounds are known in the art. In general such prior art processes suffer from one or more limitations such as excessive cracking, undesirable polymerization or unfavorable economics. While catalysts for such reactions are normally selected so as to reduce excessive cracking and undesirable polymerization, these undesired reactions still occur to some extent. Also, in some cases, the temperatures necessary for the conduct of the reaction are sufficiently high as to contribute to excessive cracking and undesirable polymerization as well as excessive use of fuels for heating. Finally, the required contact time between the feed material and the catalyst is sufficiently long as to contribute to excessive cracking and undesirable polymerization.

Accordingly, it is an object of the present invention to provide an improved process for the conversion of at least one olefinic organic compound. Another object of the present invention is to provide a process for the conversion of at least one olefinic organic compound wherein the reaction temperature is decreased. Another and further object of the present invention is to provide a process for the conversion of at least one olefinic organic compound wherein the rate of reaction is increased. These and other objects and advantages of the present invention will be apparent to one skilled in the art from a study of the present disclosure, including the detailed description of the invention.

BRIEF SUMMARY OF THE INVENTION

The present invention relates to a process for the conversion of at least one olefinic organic compound, in which a catalyst, active for such conversion of an olefinic organic compound, is exposed to electromagnetic radiation and the catalyst is contacted with the olefinic organic compound at a temperature and pressure and for a time sufficient to effect such conversion. The catalyst may be pretreated by contact with ethylene, propylene and/or butene while simultaneously exposing the same to radiation and/or the olefinic organic compound, utilized as a feed material, may be pretreated by contacting the same with magnesium oxide while simultaneously exposing the magnesium oxide to electromagnetic radiation.

BRIEF DESCRIPTION OF THE DRAWINGS

FIGS. I, II and III of the drawings are plots of percent propylene conversion vs. time for the disproportionation of propylene to ethylene and butenes, under various conditions.

FIG. IV is a plot of the ratio of trans-2-butene to cis-2-butene vs. time for the isomerization of cis-2-butene to trans-2-butene.

DETAILED DESCRIPTION OF THE INVENTION

Figure 1:
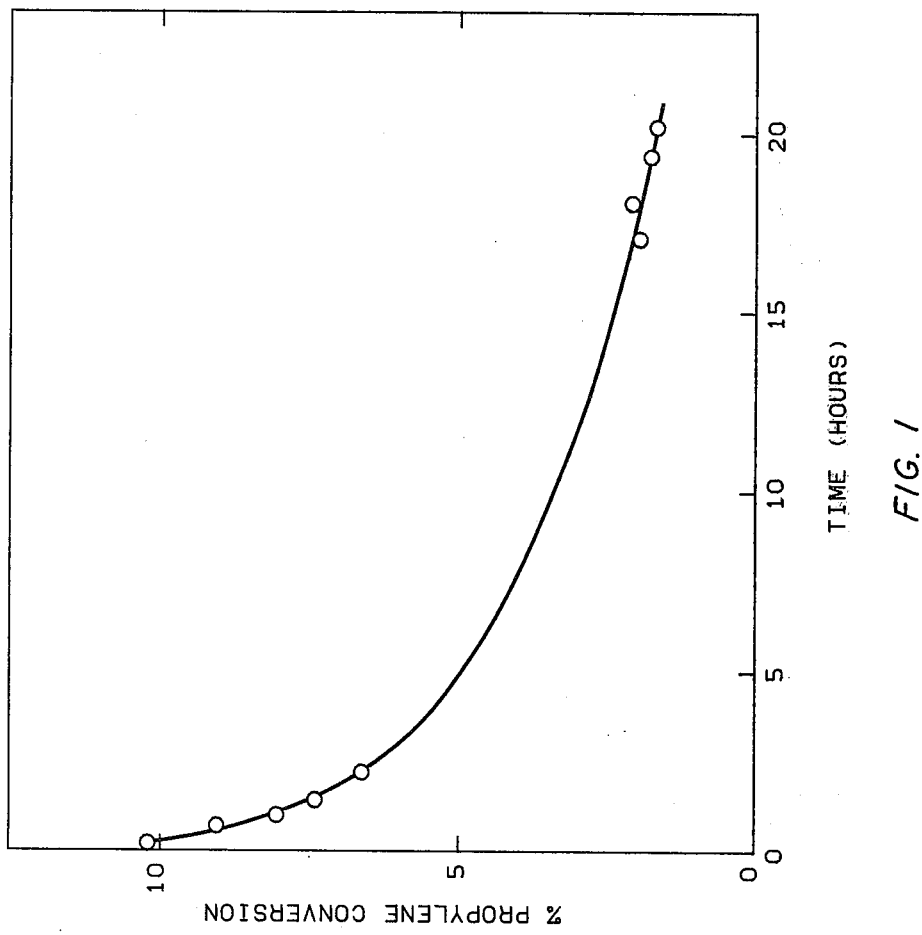
Figure 2:
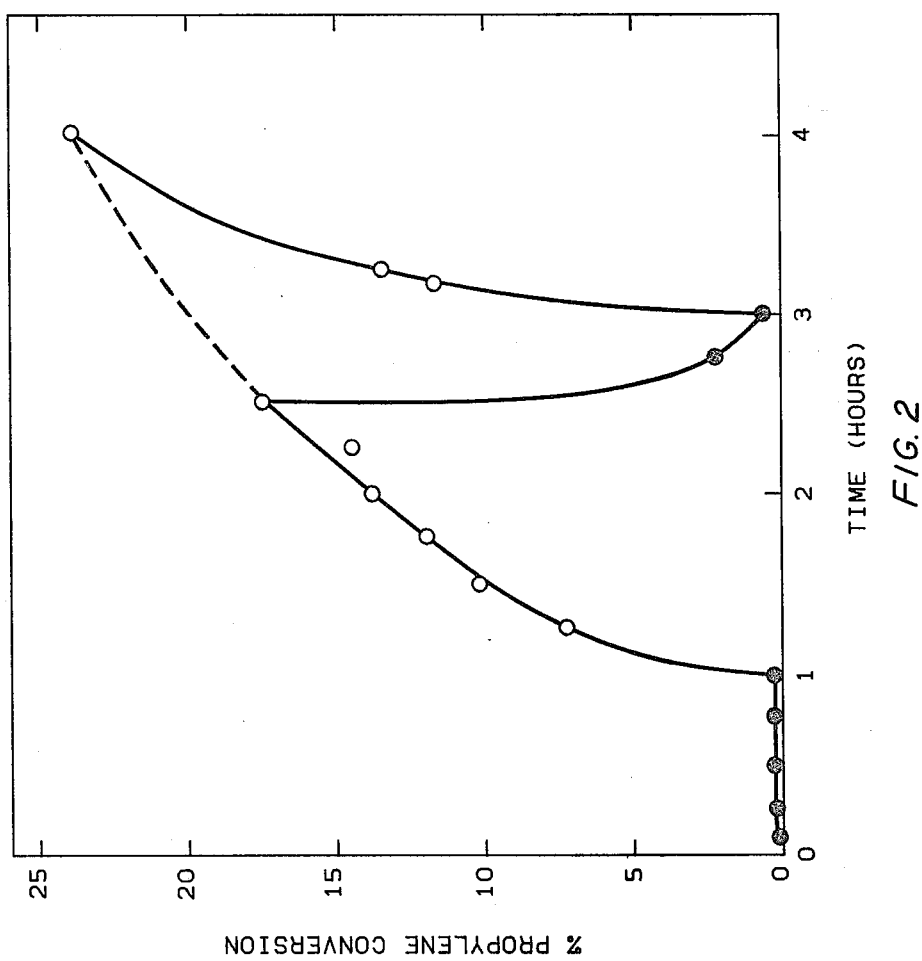
Figure 3:
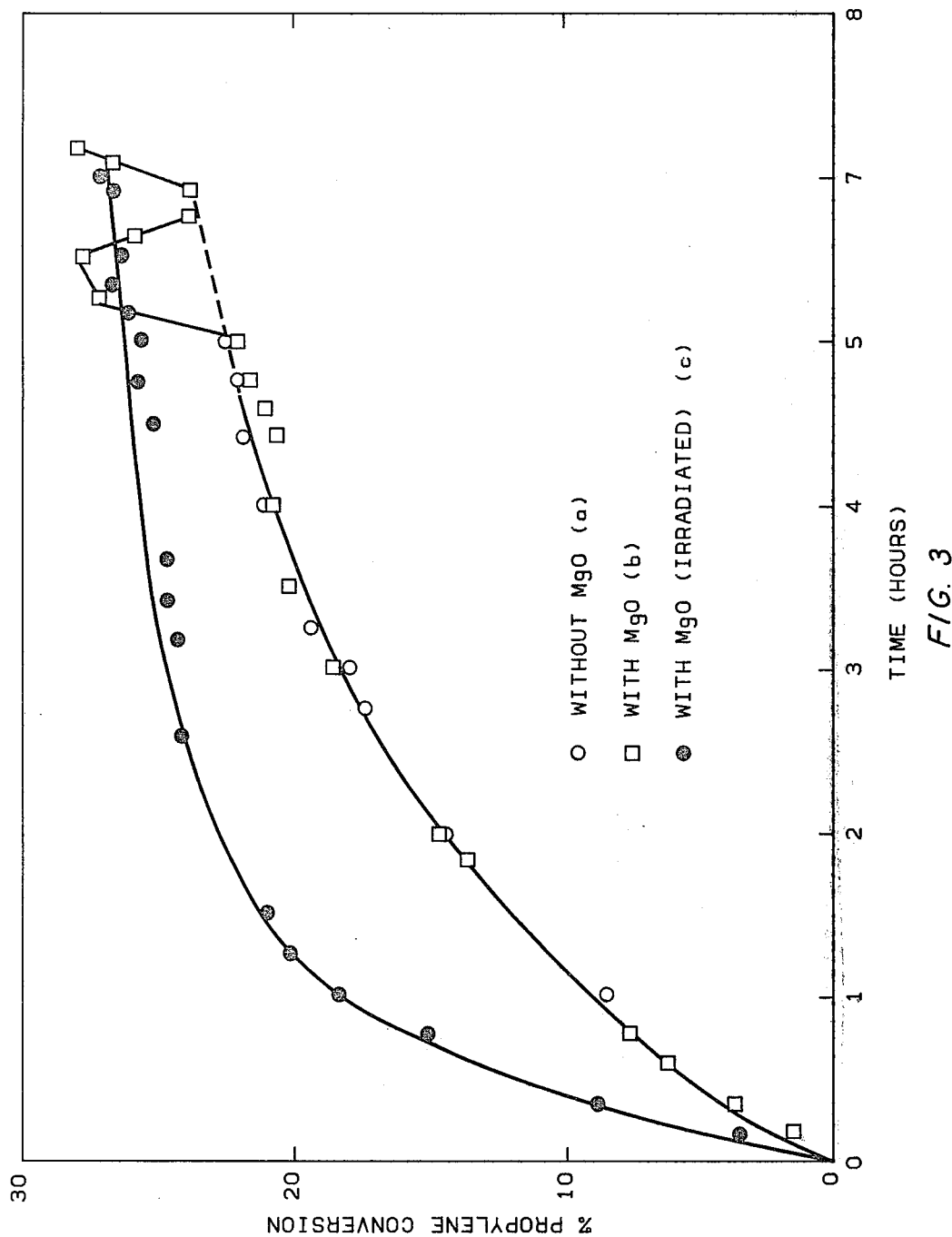
Figure 4:
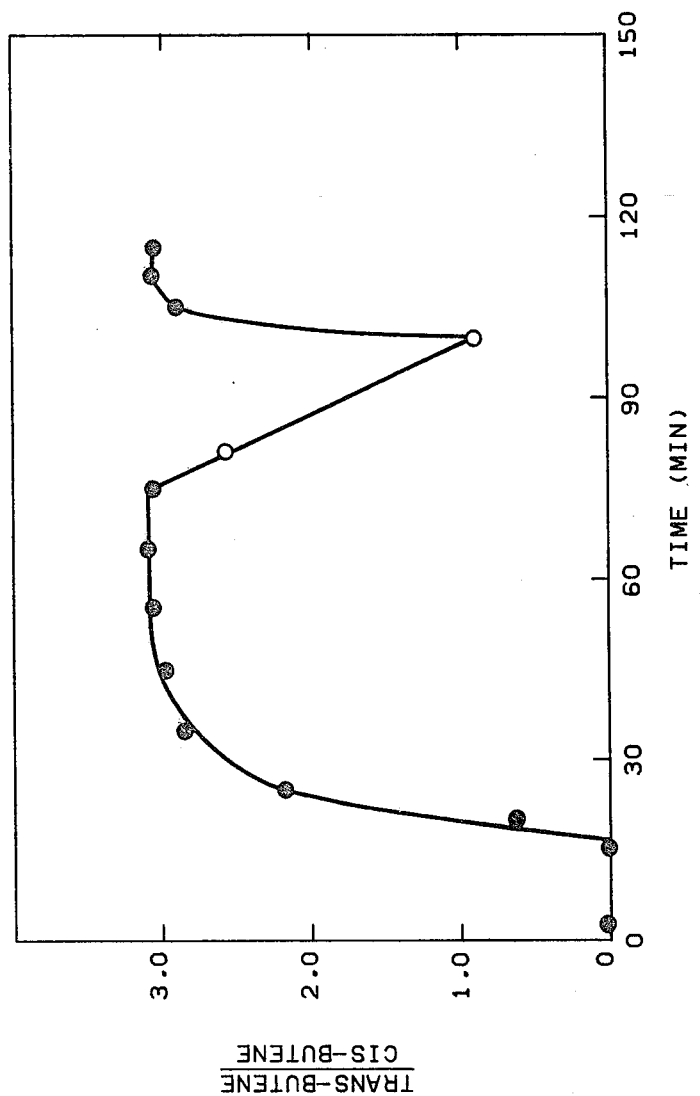

The "conversion of an olefinic organic compound", when referred to herein, includes, without limitation, the scission of a double bond and/or double bonds of one or more olefinic organic compounds and the formation of a double bond or double bonds at a different spatial position, as well as, the isomerization of at least one double bond of a single olefinic organic compound.

One such process for the conversion of olefinic organic compounds is commonly known in the art as disproportionation. In this reaction the primary reaction comprises the scission of an existing double bond between a first set of carbon atoms and a second double bond between a second set of carbon atoms and the formation of a first new double bond between the first and third carbon atoms and a second new double bond between the second and fourth carbon atoms. The first and second and the third and fourth carbon atoms can be in the same or different molecules.

This particular redistribution is illustrated by the following reactions:

(1) The disproportionation of an acyclic mono- or polyene, having at least 3 carbon atoms, into mono- or polyenes having both higher and lower numbers of carbons atoms; for example, disproportionation of propylene yields ethylene and butenes; 1,5-hexadiene yields ethylene and 1,5,9-decatriene;

(2) The conversion of an acyclic mono- or polyene having 3 or more carbon atoms and a different acyclic mono- or polyene, having 3 or more carbon atoms, to produce different olefins; for example, conversion of propylene and isobutylene to produce ethylene and isopentene;

(3) The conversion of ethylene and an internal acyclic mono- or polyene having 4 or more carbon atoms to produce other olefins having a lower number of carbon atoms than that of the acyclic mono- or polyenes; for example, the conversion of ethylene plus 4-methylpentene-2 to produce 3-methylbutene-1 and propylene;

(4) The conversion of ethylene or an acyclic mono- or polyene having 3 or more carbon atoms and a cyclic mono- or polyene to produce an acyclic polyene having a higher number of carbon atoms than that of any of the starting materials; for example, the conversion of cyclohexene and 2-butene to produce 2,8-decadiene; the conversion of 1,5-cyclooctadiene and ethylene to produce 1,5,9-decatriene;

(5) The conversion of one or more cyclic mono- or cyclic polyenes to produce a cyclic polyene having a higher number of carbon atoms than any of the starting materials; for example, the conversion of cyclopentene to produce 1,6-cyclodecadiene;

(6) The conversion of an acyclic polyene having at least 7 carbon atoms and having at least 5 carbon atoms between any two double bonds to produce acyclic and cyclic mono- and polyenes having a lower number of carbon atoms than that of the feed; for example, the conversion of 1,7-octadiene to produce cyclohexene and ethylene; or (7) The conversion of one or more cyclic polyenes having at least three carbon atoms between any two double bonds to produce acyclic and cyclic mono- or polyenes having both a higher and lower number of carbon atoms than that of feed material; for example, the conversion of 1,4-pentadiene yields 1,4-cyclohexadiene.

Another such reaction involving the conversion of one or more olefinic organic compounds is generally known in the art as proportionation. This particular reaction is essentially the reverse of disproportionation, to the extent that the reaction of a low molecular weight olefinic organic compound and a high molecular weight olefinic compound forms olefinic organic compounds of intermediate molecular weights. However, the same type of scission of double bonds and formation of new double bonds at different spatial relationships takes place. A typical reaction includes the reaction of ethylene and butene-1 to form propylene.

Yet another process involving the conversion of any olefinic organic compound is known in the art as isomerization.

In this particular reaction a single olefinic organic compound is isomerized. For example, internal olefins can be converted to a terminal olefin. Specifically, cis-2-butene can be converted to trans-2-butene. The process can also be applied to terminal olefins, such as 1-butene so as to convert at least a portion to internal olefins, such as 2-butene. A cis/trans mixture can be enriched in cis content, such as a 4/5 cis/trans 2-butene mixture can be converted to a 6/4 cis/trans mixture.

Olefinic organic compounds, suitable for use in the disproportionation type reaction, are acyclic mono- and polyenes having at least 3 carbon atoms per molecule, including the cycloalkyl and aryl derivatives thereof; cyclic mono- and polyenes having at least 4 carbon atoms per molecule, including the alkylaryl derivatives thereof; mixtures of the above olefins; and mixtures of ethylene and the above olefins. Many useful reactions are accomplished with such a cyclic olefins having 3–30 carbon atoms per molecule and with such cyclic olefins having 4–30 carbon atoms per molecule.

Some examples of acyclic olefins suitable for reactions of this type include propylene, 1-butene, isobutene, 2-butene, 1,3-butadiene, 1-pentene, 2-pentene, isoprene, 1-hexene, 1,4-hexadiene, 2-heptene, 1-octene, 2,5-octadiene, 2,4,6-octatriene, 2-nonene, 1-dodecane, 2-tetradecene, 1-hexadecene, 5,6-dimethyl-2,4-octadiene, 2-methyl-1-butene, 2-methyl-2-butene, 1,3-dodecadiene, 1,3,6-dodecatriene, 3-methyl-1-butene, 1-phenylbutene-2, 7,7-diethyl-1,3,5-decatriene, 1,3,5,7,9-octadecapentiene, 1,3-eicosadiene, 4-octene, 3-eicosene, 3-heptene, and mixtures thereof.

Some specific examples of cyclic, olefinic organic compounds, suitable for use in the disproportionation type of redistribution reaction, are cyclobutene, cyclopentene, cyclohexene, 3-methylcyclopentene, 4-ethylcyclohexene, 4-benzylcyclohexene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclododecatriene, 1,4,7,10-cyclododecatetraene, 2-methyl-6-ethylcyclooctadiene-1,4 and the like, the mixtures thereof.

Suitable isomerizable, olefinic organic compounds for use in this reaction, include acyclic monoenes and acyclic polyenes including dienes, trienes, mixtures thereof and the like. The organic feed materials can contain aryl or cycloalkyl substituents or combinations thereof. The organic compounds in this instance generally encompass compounds having from 4 to 20 carbon atoms per molecule and particularly those having 4 to 12 carbon atoms per molecule, since these are more readily available and are of greater commercial interest in an integrated oil refining chemical processing operation.

Preferred materials, because of their commercial importance, are set forth below. Examples of olefins include 1-butene, 1-pentene, 1-hexene, 3-hexene, 1-decene, 5-methyl-1-hexene, 7-methyl-1-nonene, 5-ethyl-1-octene, 2-butene, 2-pentene, 4-methyl-2-hexene, 4-phenyl-2-butene, 5-cyclopentyl-1-pentene, 4-phenyl-2-butene, 5-isopropyl-2-heptene, 2-decene, 2,3,4-trimethyl-6-dodecene, 1,3-tetradecadiene, 4-eicosene, 1-(3-butenyl)-4-ethylbenzene, 1-(3-pentenyl)-3-methylcyclopentane, 1,3-octadiene, 1,4,7-decatriene, mixtures thereof and the like.

Suitable feedstocks for the proportionation type of conversion of olefinic organic compounds include mixtures of relatively high molecular weight olefinic organic compounds and relatively low molecular weight olefinic organic compounds. For example, oil refining processes such as wax cracking and like processes, generally produce olefins having relatively high molecular weights, in the $C_{14}$ and above range, and which are of little commercial value. Similarly, olefins of relatively low molecular weight such as ethylene, propylene and butene are produced in large volume in oil refining processes. Consequently, by combining these high and low molecular weight olefins, intermediate molecular weight olefins in the $C_{10}$–$C_{16}$ range can be produced. For example, a linear $C_{23}H_{46}$ olefin and ethylene can be proportionated to produce linear $C_{12}H_{24}$ olefins which are valuable, for example, as detergent alkylates. Those materials recovered from the proportionation reaction effluent, which fall outside of the desired intermediate molecular weight range, can be recovered and recycled with the mixed feed reactants. The products of this process can also be used in producing oxo-products such as aldehydes and alcohols. Olefins available in cracked gasoline can be extracted from the gasoline and proportionated with lighter olefins or heavier olefins, from another source, to produce olefins falling within a more useful intermediate molecular weight range. Also cracked gasoline itself can be passed over the catalyst in the presence of lighter or heavier olefin feeds to produce olefins having a more desirable intermediate molecular weight for use as chemical raw materials.

Catalysts useful for the present reaction are transition metal compounds, preferably molybdenum oxide or tungsten oxide and mixtures of the same or compound of such metals convertible to oxides by calcination, deposited on an essentially inert support such as silica, alumina or silica-alumina. Some examples of such catalysts are:

(1) an oxide or compound convertible to an oxide by calcination of molybdenum, tungsten, rhenium, vanadium, niobium, tellurium, or tantalum or a sulfide of tungsten or molybdenum or a hexacarbonyl of molybdenum or tungsten on a silica base;

(2) an oxide of tungsten or molybdenum or a compound convertible to an oxide by calcination of tungsten or molybdenum or a sulfide of tungsten or molybdenum or an alkali metal salt, an ammonium salt, an alkaline earth metal salt or bismuth salt of phosphomolybdic acid or a hexacarbonyl of molybdenum or tungsten on an alumina base;

(3) any of the above catalytic materials on a silica-alumina base.

The support or base may be in any conventional form and be any conventional catalyst grade material. Some examples include precipitated gels, microspheroidal, flame hydrolyzed and aerogels.

While silica-alumina supports are known to have detrimental effects in conventional double bond redistribution reactions, such as undesired cracking and polymerization, substantially all ratios of silica-alumina can be employed in the present invention, since the temperatures employed are sufficiently low and the contact times are sufficiently short to substantially avoid these undesired reactions.

The catalysts of this invention can be prepared by incorporating the catalytic materials in the support material by conventional methods, such as impregnation, dry mixing, or coprecipitation. The finished catalyst can be in the form of powders, granules, agglomerates, pellets, spheres, extrudates and the like, depending upon the type of contacting technique employed in the reaction.

The catalysts of this invention may contain other materials which do not substantially promote unwanted reactions. For example, the base may contain substantial amounts of inert materials. However, when molybdenum oxide is utilized on an alumina support or a silica-alumina support predominating in alumina, cobalt oxide, which is normally inert, has a promoting affect for a redistribution reaction and, accordingly, can be used in amounts up to about 20% of the total support.

The amounts of catalytic material employed are generally in the range of about 0.1 to 30 percent by weight of the total catalyst composition and preferably about 0.3 to 15 percent by weight of the total composition. Good results have been obtained with about 0.3 to 2.5 percent tungsten oxide, based on the weight of the total composition.

The composite catalysts are activated by heating in air or in an oxygen-containing atmosphere, preferably free from reducing gases, for about 0.5 to 20 hours or longer at temperatures ranging from about 700° to 1600° F. and preferably about 900° to 1400° F.

The present reaction can be carried out either batchwise or continuously, using a fixed catalyst bed, a stirred batch reactor, a fluidized catalyst bed, or other conventional contacting techniques. The feed material can be utilized either with or without a diluent. Diluents selected from the group consisting of paraffinic and cycloparaffinic hydrocarbons can be employed. Sample diluents are propane, cyclohexane, methylcyclohexane, normal pentane, normal hexane, isooctane, dodecane, and the like or mixtures thereof, including, primarily those paraffins such as cycloparaffins having up to about 12 carbon atoms per molecule. The diluent should not be reactive under the conditions employed.

The feed materials may be in the vapor or liquid phase and pressures in a range of about 0 to 500 psia may be employed, preferably ambient pressure, with the reaction time in the range of about 0.1 seconds to 10 hours.

As previously pointed out, the practice of this invention permits one to operate at temperatures substantially below those normally employed in this type of reaction. For example, the temperature employed will be in the range of about 0° to 500° C. and preferably about 0° to 300° C. Reactions at ambient temperature have been quite effective. As will be pointed hereinafter in the specific examples, it has been found that without ultraviolet radiation the disproportionation reaction does not occur at temperatures below about 300° C. when a $WO_3$-$SiO_2$ catalyst is utilized. Where an isomerization type of reaction is employed, the temperature may be as low as −20° C.

With a fixed reactor bed and continuous operation, gas hourly space velocities (GHSV) in the range of about 50 to 50,000 parts by volume of hydrocarbon per part by volume of catalyst per hour are suitable.

It has been found in accordance with the present invention that if the reaction is carried out, as previously outlined, while the catalyst is exposed to electromagnetic radiation above 1000A°, the reaction time can be substantially reduced and the temperature can be reduced, thus eliminating substantially all side reactions and increasing production of the desired materials. The electromagnetic radiation to the reaction zone can be supplied by commercially available photochemical mercury arc lamps, such as those sold by General Electric and Ultraviolet Products, Inc. The lamps are placed in the vicinity of the reactor in the manner conventionally employed in the art. (About 2 to 4 centimeters from the center of the bed, preferably 3.5 centimeters from the center.) Medium pressure mercury arc lamps are exemplary of suitable lamps operable in the instant invention. The radiation generated from such lamps typically has wavelengths of 2537, 3130, 3650, 4047, 4358, 5461 and 5780 Angstroms. Since ultraviolet radiation is considered to be in the range of about 1000 to 4000 Angstrom units, then the first three wavelengths mentioned will produce ultraviolet radiation which has been found particularly useful. However, radiation above 4000 Angstroms can be utilized. Low pressure lamps suitable for the practice of the present invention are characterized by relatively little heat evolution during operation and almost exclusive generation of the 2537 Angstroms spectral line. Other suitable lamps include hot cathode (germicidal lamps) and cool cathode (sterilamps) which provides sources of the 2537 Angstrom spectral line. It has been found that the effect of the electromagnetic radiation is not one of supplying heat but is simply that of light radiation.

It has also been found that the exposure to electromagnetic radiation can be carried out either continuously or intermittently. As hereinafter shown by the examples, if the catalyst is irradiated in the presence of an olefin, either the feed olefin or another, prior to contact of the reaction, the catalyst becomes activated. Thereafter, the activity degenerates at a relatively slow rate. Hence such a pretreatment can be carried out, the radiation stopped and the reaction with the selected feed carried out. Thereafter, the desired level of catalyst activity may be maintained by periodic exposure to radiation.

Additionally, it has been found, in accordance with the present invention, that the catalyst may be pretreated by exposing the catalyst to radiation in the presence of ethylene, butene and/or propylene. The effect of pretreatment with propylene during radiation was found to be more beneficial in activating the catalyst for subsequent disproporationation.

It further been found, in accordance with the present invention, that the feedstock may be pretreated by contact with magnesium oxide prior to contact with the catalyst for the conversion of olefinic organic compounds. Such contact may be carried out conveniently by placing a bed of magnesium oxide head of a bed of the catalyst. Significant improvement is obtained by irradiating both the magnesium oxide bed and the catalyst bed.

3.5 cm. (2 cm. from the wall of the quartz heater.) The following results were obtained:

TABLE I

| Time on Stream Minutes | Temp. °C. | UV Light Source | Disproportionation Conversion, % | Effluent Analysis, Wt. % | | | | |
|---|---|---|---|---|---|---|---|---|
| | | | | Ethylene | Propylene | 1-Butene | Trans 2-Butene | Cis 2-Butene |
| 80 | 400 | on | 4.1 | 1.4 | 95.9 | 0.2 | 1.3 | 1.2 |
| 95 | 400 | off | 2.2 | 0.74 | 97.8 | 0.11 | 0.68 | 0.66 |
| 155 | 350 | on | 1.8 | 0.64 | 98.2 | 0.06 | 0.54 | 0.61 |
| 170 | 350 | off | 0.2 | 0.07 | 99.8 | 0.01 | 0.08 | 0.07 |
| 183 | 300 | on | 1.3 | 0.45 | 98.7 | 0.04 | 0.41 | 0.44 |

The following examples will specifically demonstrate the practice of the present invention and its advantages. It is to be understood that these examples are utilized merely for illustrative purposes and are not to be considered as limitations of the invention.

EXAMPLE 1

The catalyst was prepared by impregnating dried, 20 to 40 mesh silica gel with a sufficient quantity of an aqueous solution of ammonium metatungstate to give the quivalent of 5 weight percent $WO_3$ based on the weight of the dried total catalyst. The resulting paste was thoroughly mixed, additional water added to the paste and the mixture was again well mixed. It was then slowly dried on a hot plate until free flowing particles having a constant weight were obtained.

One cc of the catalyst was placed in a 7 mm. I.D. tubular quartz reactor containing an internal thermocouple well. The reactor was heated with an electric furnace constructed of quartz tubing to allow passage of UV light from an exterior source to the interior of the reactor. Provisions were made to allow entry of fluids such as air, nitrogen and feedstocks into the reactor and the removal of effluent materials. The effluent was analyzed by means of gas-liquid chromatography.

The catalyst was activated by heating the reactor containing it to 600° C. while passing dry air over it. It was flushed with nitrogen for 15 minutes while it was cooled to 400° C. Propylene was passed over the catalyst at atmospheric pressure and at a rate of 11.6 cc gas/minute (about 696 GHSV [gas hourly space velocity]) while the catalyst was periodically irradiated with a General Electric H 100A 38-100 watt lamp. The distance of the lamp to the center of the catalyst bed was These data show increased disproportionation of propylene to ethylene and butenes when the catalyst is being irradiated with UV light compared to the results obtained in the absence of the radiation. The data show disproportation occuring even at 300° C. while the catalyst is irradiated, but little disproportionation occurs at 350° C. when the catalyst is not irradiated.

EXAMPLE 2

The catalyst used in Example 1 was regenerated by passing dry air over it, while it was disposed in the reactor, for 1.5 hours while maintaining a temperature of 600° C. It was then flushed with nitrogen for 20 minutes, while the reactor and its contents were cooled to 300° C. Propylene was passed over the catalyst at the rate of 10 cc/minute during periodic irradiation with UV light, as in Example 1. The following results were obtained:

TABLE II

| Time on Stream Minutes | Temp. °C. | UV Light Source | Disproportionation Conversion, % | Effluent Analysis, Wt. % | | | | |
|---|---|---|---|---|---|---|---|---|
| | | | | Ethylene | Propylene | 1-Butene | Trans 2-Butene | Cis 2-Butene |
| 15 | 300 | off | 0.0 | — | 100.0 | — | — | — |
| 35 | " | on | 0.9 | 0.31 | 99.1 | 0.02 | 0.28 | 0.29 |
| 73 | " | on | 1.8 | 0.60 | 98.3 | 0.03 | 0.52 | 0.55 |
| 87 | " | off | trace (<0.05) | trace | 99.96 | none | 0.02 | 0.02 |
| 160 | " | off | " | " | " | " | " | " |
| 185 | " | lamp turned on | | | | | | |
| 245 | " | on | 2.4 | 0.88 | 97.5 | 0.04 | 0.76 | 0.79 |
| 260 | 250 | on | 1.1 | 0.40 | 98.9 | 0.02 | 0.35 | 0.37 |
| 287 | 200 | on | 1.0 | 0.34 | 99.0 | trace | 0.31 | 0.33 |
| 305 | 160 | on | 1.6 | 0.56 | 98.4 | none | 0.49 | 0.53 |
| 360 | 115 | on | 1.4 | 0.50 | 98.6 | none | 0.45 | 0.47 |

The results show continuing disproportionation activity as the temperature is reduced from 300° C. to 115° C. when the catalyst is being irradiated. In the absence of such radiation, no disproportionation activity was observed even at 300° C.

EXAMPLE 3

One cc of the 5 weight percent $WO_3$ on silica catalyst was placed in the reactor and the reactor heated to 600° C. Dry air was passed over the catalyst for one hour, then the catalyst was flused with nitrogen for 30 minutes while the temperature was reduced to 500° C. Propylene was passed over the catalyst at the rate of 10 cc/minute for 1 hour at 500° C. The temperature was then gradually reduced to 25° C. The following results were obtained:

TABLE III

| Time on Stream Minutes | Temp. °C. | UV Light Source | Disproportionation Conversion, % | Percent 1-Butene In Butenes Fraction | Inert Gases Air, CH$_4$ | Effluent Analysis, Wt. % | | | | |
|---|---|---|---|---|---|---|---|---|---|---|
| | | | | | | Ethylene | Propylene | 1-Butene | Trans 2-Butene | Cis 2-Butene |
| 25 | 500 | off | 43.5 | 18.0 | 0.1 | 17.3 | 56.3 | 4.7 | 12.4 | 9.0 |
| 70 | 400 | " | 1.9 | 4.6 | 0.04 | 0.7 | 97.96 | 0.06 | 0.67 | 0.57 |
| 85 | 300 | " | 0.1 | —** | 0.04 | 0.03 | 99.87 | — | 0.07 | — |
| 100 | 25 | " | 0.0 | — | 0.04 | — | 99.71* | — | 0.02 | — |

*Detected 0.23 wt. % isobutane also
**Dash indicates none detected or a trace

The furnace was removed and a cylindrical photochemical lamp (Ultraviolet Products, Inc.) was placed around the reactor. The lamp produces an intensity of 30,000 microwatts/cm$^2$ of 2537 Angstroms radiation in the axis of its cylindrical cavity where the catalyst was located. The following results were obtained:

TABLE IV

| Time On Stream Minutes | Temp. °C. | UV Light Source | Disproportionation Conversion, % | Inert Gases Air, CH$_4$ | Effluent Analysis, Wt. % | | | |
|---|---|---|---|---|---|---|---|---|
| | | | | | Ethylene | Propylene | Trans 2-Butene | Cis 2-Butene |
| 101 | 38 | on | — | — | — | — | — | — |
| 115 | 38 | " | 5.0 | 0.03 | 1.8 | 95.1 | 1.8 | 1.3 |
| 175 | 38 | " | 14.1 | 0.03 | 5.0 | 85.8 | 5.9 | 3.2 |
| 234 | 38 | " | 18.4 | 0.04 | 6.5 | 81.6 | 8.0 | 3.8 |
| 295 | 38 | " | 19.4 | 0.03 | 6.8 | 80.5 | 8.6 | 4.0 |
| 352 | 38 | " | 20.2 | 0.04 | 7.1 | 79.8 | 9.0 | 4.1 |
| 382 | 38 | " | 20.4 | 0.04 | 7.1 | 79.6 | 9.1 | 4.2 |
| 383 | | | lamp off, propylene rate reduced to 9 cc/minute | | | | | |
| 497 | 28 | off | 8.1 | 0.05 | 2.8 | 91.9 | 3.2 | 2.1 |
| 557 | 24 | " | 6.4 | 0.04 | 2.2 | 93.6 | 2.4 | 1.7 |
| 1445 | 23 | " | 1.6 | 0.04 | 0.6 | 98.4 | 0.4 | 0.5 |
| 1467 | 40 | " | 5.0 | 0.04 | 1.8 | 95.0 | 1.7 | 1.4 |
| 1488 | 40 | " | 3.3 | 0.04 | 1.2 | 96.7 | 1.1 | 1.0 |
| 1505 | 60 | " | 1.2 | 0.04 | 0.4 | 98.8 | 0.3 | 0.4 |
| 1520 | 80 | " | 0.1 | 0.04 | 0.12 | 99.9 | 0.02 | — |

The results show high conversions of propylene to ethylene and 2-butenes at low temperatures in the pesence of UV radiation of the intensity and wavelength properties previously described. Since double bond isomerization of 2-butenes to 1-butene is essentially lacking it is apparent that low temperature disproportionation of propylene under the stated conditions results in high selectivities to 2-butenes. Inspection of the data also revels that substantial disproportionation activity still lingers after turning off the lamp. In fact, a little disproportionation was still occurring after the lamp was off for 1137 minutes (almost 19 hours). This suggests intense irradiation of the catalyst enhances its capability for disproportionation but that the capability decays fairly rapidly with the passge of time.

In the previous examples a research grade propylene was used. It was found that this material was prepared without taking precautions to exclude air, hence the conversions were lower than normal. In the examples which follow, a polymerization grade propylene, which is essentially free of air, was utilized and, for comparative purposes, propylene from the same cylinder was used.

Except where indicated otherwise, the following apparatus and procedures were utilized in the examples below.

All runs were made in tubular (7 mm inside diameter) quartz reactor. The reactor was equipped with an internal thermocouple well and the temperature was measured in the center of the catalyst bed. The reactor was equipped with a quartz heater so that it could be heated simultaneously with exposure of the catalyst to irradiation. The reactor was also equipped with a low pressure short wave ultraviolet light manufactured by Ultra-Violet Products, Inc. (model PCOX1). This unit consists of four circular lamps enclosed by a cylindrical reflector, thus providing uniform illumination of a cylindrical cavity 3 inches in diameter and 5 inches long. The unit produces an intensity of 30,000 microwatts/cm.$^2$ of 2537 Angstroms radiation in the axis of its cylindrical cavity. The unit was arranged so that its axis coincided with the axis of the catalyst bed.

The catalyst support was a Davison silica hydrogel calcined in air to constant weight at 500° to 550° C. and had the following properties:
surface area—246 m$^2$/g
pore volume—1.6 cc/g
pore diameter —260 A°
mesh size—20–40

This support was impregnated with an aqueous solution of ammonium metatungstate, dried to constant weight at 120° C. and calcined in air at 600° C. to produce a finished catalyst having 2.5% by weight of tungsten oxide, based on the total weight of the catalyst.

0.5 grams of the catalyst was disposed as a fixed bed in the reactor.

The catalyst was activated in air at 600° C. for at least one hour, flushed with N$_2$ at 500° C. for 20 minutes or more and cooled to the desired temperature for the test under N$_2$. The propylene feed was passed through molecular sieves and magnesium oxide columns before entering the reactor.

All tests were conducted at atmospheric pressure.

The resultant products of the tests were analyzed by vapor phase chromatography, using a 20 foot bis [2-(2-methoxyethoxy)ethyl] ether column.

EXAMPLE 4

Since an initial induction period prior to maximum production was observed in prior propylene disproportionation tests, it was thought that this period might be eliminated by prereducing the catalyst. In a first test, after activation of the catalyst, the catalyst was reduced with propylene at 450° C. for 3.5 hours and then cooled to ambient temperature under a stream of propylene. Propylene was then passed thru the bed of catalyst at a rate of 600 GHSV while irradiating the catalyst and maintaining a temperature of 36° C. Similarly, the catalyst was prereduced with $H_2$ at 450° C. for one hour. In a parallel test, the catalyst was cooled to ambient temperature under $N_2$ (nonprereduced). It was found that the induction period and the ultimate production were substantially the same in all tests, thus indicating that prereduction of the catalyst made no apparent difference.

EXAMPLE 5

In order to determine the effect of weight % tungsten oxide concentration in the $WO_3$-$SiO_2$ catalyst on conversion, a series of catalysts, having the concentrations indicated in the table, were prepared. Propylene was passed through the catalyst at 700 GHSV while irradiating the catalyst and maintaining a temperature of 36° C. The mol percent conversion of propylene is listed in the table as a function of catalyst concentration and time.

TABLE 5

| Wt. % $WO_3$ | Time on Stream in Hours | | | | |
|---|---|---|---|---|---|
| | 1 | 2 | 3 | 4 | 5 |
| 0.16 | 6.1 | 9.1 | 10.5 | — | — |
| 0.7[a] | 9.5 | 16.3 | 19.1 | 21.0 | 22.2 |
| 0.8 | 17.4 | 25.0[c] | 27.1 | 29.0 | 29.6 |
| 2.5[b] | 19.8 | 25.0 | 28.6 | 30.0 | 30.3 |
| 10.0 | 15.0 | 19.0 | 22.0 | 23.0 | 23.9 |

[a]Catalyst prepared by impregnation with $Na_2WO_3$.
[b]600 GHSV.
[c]Value obtained by interpolation.

It is to be observed, from the above, that conversion increased with increasing $WO_3$ concentration, up to about a 2.5 weight % tungsten oxide concentration, but then essentially levelled off and decreased at 10.0 weight %.

For comparative purposes the same catalysts were tested without irradiation at a rate of 700 GHSV while maintaining a temperature of 450° C. The steady state mol % propylene conversion resulting from these tests is listed in the table and compared with the previous conversion under irradiation at 3 hours on stream.

TABLE VI

| Wt. % $WO_3$ | Mol % Propylene Conversion | |
|---|---|---|
| | w/o irradiation | w/radiation |
| 0.16 | 0.4 | 10.5 |
| 0.8 | 4.3 | 27.1 |
| 2.5 | 25.0 | 28.6 |
| 10.0 | 45.0 | 22.0 |

It is clear from these tests that, without irradiation, conversion continues to increase with increasing $WO_3$ concentrations as high as 10 weight % $WO_3$.

EXAMPLE 6

In order to determine the effects of preirradiation of the $WO_3$-$SiO_2$ catalyst, the catalyst (0.8 weight % $WO_3$) was irradiated at 36° C. under a stream of propylene for 200 minutes. The light source was then turned off and propylene was passed through the catalyst at a rate of 660 GHSV at ambient temperature (20° to 25° C.) FIG. 1 of the drawings shows mol % propylene conversion as a function of time after the light was turned off.

FIG. 1 illustrates that catalyst activity declines with time after a period of preirradiation and that some activity still exists after 20 hours on stream.

In parallel tests, the catalyst was preirradiated under 2-butene, ethylene and $N_2$, respectively. Results similar to those of FIG. I were obtained using 2-butene and ethylene, but no activity was observed using $N_2$.

EXAMPLE 7

Utilizing the catalyst used in the previous examples, and a feed rate of 1000 GHSV while maintaining a temperature of 300° C. (the temperature at which the catalyst begins to exhibit activity without irradiation), a test was run to illustrate the comparative effect of irradiation versus nonirradiation at this temperature. The light was initially off, was turned on at 1 hour, turned off at 2.5 hours and was turned on again at 3 hours. The results are shown in FIG. II of the drawings, where mol % propylene conversion is plotted against time on stream.

EXAMPLE 8

Previous work indicated that disproportionation of propylene, under irradiation, showed an Arrhenius temperature dependence from 36° C. to about 100° C., declined from 100° C. to about 250° C. and then increased above 250° C. This behavior suggested that catalyst activity at higher temperatures was retarded by some form of in situ poisoning. Accordingly, a series of tests were conducted, utilizing a bed of magnesium oxide upstream of the catalyst bed. In these tests 1.5 ml of MgO (20/40 mesh) were placed in the reactor above the catalyst and separated therefrom by a plug of quartz wool. A 2.5 weight % $WO_3$ on $SiO_2$ catalyst was used at a propylene feed rate of 20 ml/min while maintaining a temperature of 36° C. In a first test (a), only the $WO_3$-$SiO_2$ catalyst was irradiated. A second test (b) was run, while irradiating only the $WO_3$-$SiO_2$ catalyst for the first 5 hours, thereafter irradiating both the MgO and the $WO_3$-$SiO_2$ catalyst, discontinuing irradiation of the MgO at 5.5 hours and again irradiating the MgO at about 5.9 hours. Finally, in a third test (c), both the MgO and $WO_3$-$SiO_2$ catalyst were irradiated throughout the test.

The results of this series of tests are shown in FIG. III of the drawings, which illustrates a substantial improvement in conversion of propylene when irradiating a MgO guard chamber even at 36° C. Under the same conditions no propylene conversion was obtained when a bed of irradiated MgO was utilized without a $WO_3$-$SiO_2$ catalyst.

EXAMPLE 9

In order to determine the degree of polymerization occurring during irradiation, a series of tests were run in which propylene was passed through the hereinafter specified solid contact material. After discontinuance of the propylene feed, the contact material was flushed with $N_2$ at ambient temperature and transferred to a quartz bulb, which was connected to a vacuum system. The bulb was evacuated and the temperature of the contact material was raised stepwise to 300° C. Gases desorbed from the contact material at the various temperatures were analyzed in an Extranuclear quadrupole mass spectrometer. The degree of polymerization of the desorbed species was determined from the peak of highest mass number observed in the mass spectrum.

In two tests, propylene was passed through a 2.5 weight % $WO_3$ on silica catalyst (prereduced at 450° C. with $H_2$) at a rate of 1200 GHSV for 4 hours at 36° C. In one instance the catalyst was irradiated and in the other it was not. The non-irradiated catalyst was inactive for propylene conversion and the gases thereafter desorbed from the catalyst had a maximum mass number of 84 (corresponding to a $C_6$ species). The irradiated catalyst converted 13 mol % of the propylene at 4 hours on stream and the gases, desorbed from the catalyst, had a maximum mass number of 110 (corresponding to a $C_8$ species).

In a second set of tests, propylene was passed through a silica support alone and through a 0.7 weight % $WO_3$ on silica catalyst, respectively, (without prereduction) at 700 GHSV and under irradiation at 36° C. The maximum mass number for silica alone was 84 and that for $WO_3$ on silica was 110.

In a third test propylene was passed through a 5 weight % $WO_3$ on silica catalyst at 400° to 500° C. Polymeric material was found on the catalyst and the highest mass number was 190 (the upper limit of the instrument).

The results of this series of tests thus indicated that some polymerization takes place at 36° C. on both the silica support and the $WO_3$ on silica catalyst. However, irradiation does not increase polymerization. On the other hand, at 400° to 500° C. substantial polymerization occurs. It should be noted, however, that no compounds having more than 4 carbon atoms were detected in the effluent and the polymeric materials reported were those desorbed from the catalyst.

EXAMPLE 10

A liquid phase reaction was carried out in this test. 0.4 g of a 2.5 weight % $WO_3$ on silica catalyst was activated, charged to a reactor, heated to 600° C., dry air passed over it for 1 hour, flushed with nitrogen for 1 hour at 500° C., cooled to 25° C. under $N_2$ and the nitrogen evacuated. The catalyst was transferred to a 425 cc quartz, batch reactor under argon. 2 cc of pentenes (96% cis and 4% trans) and 18 ml of cyclohexene were added to the reactor which was sealed with a neoprene cap. The mixture was irradiated while stirring with a magnetic stirrer at ambient temperature. Samples were removed from the liquid phase at various intervals and analyzed by gas/liquid chromatography over a 15 ft. ethyl adipate column. The results were as follows:

TABLE VII

| Time in Minutes | 2-butene | | 2-pentene | | 3-hexene | |
|---|---|---|---|---|---|---|
| | trans | cis | trans | cis | trans | cis |
| 0 | 0 | 0 | 4.1 | 95.9 | 0 | 0 |
| 20 | 0.56 | 1.2 | 6.8 | 88.4 | 1.6 | 1.5 |
| 60 | 1.9 | 3.7 | 12.6 | 71.6 | 5.5 | 4.8 |
| 130 | 5.3 | 7.3 | 24.2 | 36.9 | 17.5 | 8.7 |

The above results are not quantitative due to substantial losses of butenes to the vapor phase. However, only butenes and hexenes were observed as products and the tests clearly demonstrate the selective conversion of 2-pentenes to 2-butenes and 3-hexenes.

EXAMPLE 11

The disproportionation of 1,5-hexadiene was studied, utilizing a 10 weight % $WO_3$ on $SiO_2$ catalyst (prereduced with $H_2$ at 500° C.). A mixture of 0.4 g catalyst, 2 cc of 1,5-hexadiene and 18 cc of cyclohexene was irradiated and stirred in the above-mentioned reactor for 10 hours. The following products were detected in the liquid phase:

TABLE VIII

| | Wt. % |
|---|---|
| 1,5-hexadiene | 13.6 |
| trans-1,5,9-decatriene | 11.2 |
| cis-1,5,9-decatriene | 2.4 |
| $C_{15}$ | 25.8 |
| $C_{20}$ | 19.7 |
| $C_{25}$ | 15.9 |
| $C_{30}$* | 11.4 |

*Compounds above $C_{30}$ were not measured.

EXAMPLE 12

Redistribution of double bonds by isomerization is demonstrated in this example. Cis-2-butene was passed through a 0.8 weight % $WO_3$ on $SiO_2$ catalyst at a rate of 20 cc gas/min. The results are tabulated below:

TABLE IX

| Time in Minutes | Temp. °C. | Conditions of Light Source | % Conversion to trans-2-butene |
|---|---|---|---|
| 15 | 23° | off | 0 |
| 15 | 23° | turned on | |
| 30 | 36° | on | 72 |
| 45 | 36° | on | 74 |

No products other than 2-butenes were observed.

In another test, cis-2-butene was passed through 1 cc of activated MgO at 900 GHSV at 25° C. (less than 2% conversion to 1-butene) and thence through a 2.5 weight % $WO_3$ on $SiO_2$ catalyst while turning the light source on at 15 minutes, off at 75 minutes and on again at 100 minutes. The results are plotted as the ratio of trans- to cis-butenes versus time in FIGURE IV of the drawings, the maximum ratios being the equilibrium ratio. The 1-butene was consumed by reaction with 2-butene to yield propylene and 2-pentene.

EXAMPLE 13

Because the decline in conversion after irradiation, reported in Examples 3 and 6, could be caused by poisoning of the catalyst, a test was conducted in which special precautions were taken to minimize the presence of impurities in the feed stream. The standard brass regulator on the feed tank, used in all other tests, was replaced with an ultrasonically cleaned stainless steel regulator. The propylene was passed through a column of molecular sieve, a column of activated BASF catalyst (30% copper), and a column of magnesium oxide. To minimize air leaks into the reactor the test was conducted at 1.4 atm (6 psig).

One cc (0.4 gram) of 25% $WO_3$-$SiO_2$ was used. This catalyst was prepared by impregnation of Davison grade 59 silica with ammonium metatungstate. Propylene flow rates were varied during the test, but all data reported below were measured at 3300 GHSV, so that conversion levels below 10% could be maintained at ambient temperature.

The test was conducted over a 30 day period during which the catalyst was irradiated three times: (a) initially for 7.25 hours, (b) after 2 days for 6 hours, and (c) after 17 days for 1 hour. Details are given below:

(a) 0 Time on Stream: After the catalyst was activated in air at 600° C. and flushed with nitrogen, the furnace was removed and the catalyst was irradiated under a stream of propylene at 31° C. for 7.25 hours. The light source was then turned off, the propylene flow was stopped and nitrogen was passed over the catalyst at ambient temperature for 14 hours. When propylene was reintroduced onto the catalyst, conversion was 3.7% and remained unchanged after 9 hours. The catalyst was again flushed with $N_2$ for 13 hours, after which time propylene conversion was 3.4%. (b) 2 Days on Stream: The catalyst was irradiated under propylene for 6 hours. After irradiation, the following conversions were observed:

| Time After Irradiation | Temp. (°C.) | % |
|---|---|---|
| 0 | 21.5° | 8.2 |
| 21 min. | 21° | 7.8 |
| 1 hour | 21° | 7.5 |
| 2 hours | 21° | 7.4 |
| 2.5 hours | 21° | 7.3 |
| 2.5 hours | Propylene flow interrupted. Nitrogen passed over the catalyst for 5.6 days. | |
| 137 hours (5.7 days) | 21° | 3.0 |
| | Catalyst kept under a slow stream of propylene except during measurements | |
| 281 hours (11.7 days) | 21° | 2.8 |
| 359 hours (15 days) | 21° | 2.8 |

(c) 17 Days on Stream: The catalyst was irradiated for 1 hour under propylene. Thereafter, the catalyst was kept under a slow stream of propylene. Conversions were measured at 3300 GHSV.

| Time After Irradiation | Temp. °C. | % Conv. |
|---|---|---|
| 13 min. | 21 | 6.2 |
| 47 hrs. (~2 days) | 22 | 4.7 |
| 92 hrs. (~4 days) | 22 | 4.2 |
| 307 hrs. (~13 days) (30 Days on Stream) | 22 | 3.2 |

While specific examples of materials, equipment and procedures have been set forth above, it is to be understood that such designations are by way of illustration only and are not to be considered limiting. Accordingly, the present invention is to be limited only by the appended claims.

I claim:

1. In a process for the redistribution of at least one olefinic bond of at least one reactant olefinic organic compound which comprises reacting said at least one reactant olefinic organic compound in the presence of a solid catalyst comprising a compound selected from the group consisting of transition metal oxides, transition metal compounds convertible to oxides by calcination and mixtures thereof deposited on an essentially inert solid support, at a temperature, at a pressure and for a time sufficient to effect said redistribution of at least one olefinic bond, the improvement comprising; exposing said solid catalyst to electromagnetic radiation having a wavelength of at least about 1000 Å in the presence of at least one olefinic organic compound selected from the group consisting of at least one reactant olefinic organic compound, at least one olefinic organic compound other than a reactant olefinic organic compound and mixtures thereof, said exposing of said solid catalyst to electromagnetic radiation being carried out prior to said reacting of said at least one reactant olefinic organic compound, during said reacting of said at least one reactant olefinic organic compound or both prior to and during said reacting of said at least one reactant olefinic organic compound.

2. A process in accordance with claim 1 wherein the process comprises converting at least one reactant olefinic organic compound, having at least 3 carbon atoms per molecule, to at least one product olefinic organic compound having a larger number of carbon atoms per molecule than said reactant olefinic organic compound and at least one product olefinic organic compound having a smaller number of carbon atoms per molecule than said at least one reactant olefinic organic compound.

3. A process in accordance with claim 2 wherein the reactant olefinic organic compound is propylene, the at least one product olefinic organic compound having a larger number of carbon atoms per molecule than said reactant olefinic organic compound is butene and the at least one product olefinic organic compound having a smaller number of carbon atoms per molecule than said reactant olefinic organic compound is ethylene.

4. A process in accordance with claim 2 wherein the reacting of the at least one olefinic organic compound is carried out at a temperature between about 0° C. and 500° C.

5. A process in accordance with claim 4 wherein the reacting of the at least one olefinic organic compound is carried out at a temperature of about ambient temperature.

6. A process in accordance with claim 2 wherein the reacting of the at least one reactant olefinic organic compound is carried out at a pressure between about 0 and 500 psia.

7. A process in accordance with claim 6 wherein the reacting of the at least one reactant olefinic organic compound is carried out at a pressure of about ambient pressure.

8. A process in accordance with claim 2 wherein the reacting of the at least one reactant olefinic organic compound is carried out at a gas hourly space velocity between about 50 and 50,000 parts by volume of said at least one reactant olefinic organic compound per part by volume of the solid catalyst per hour.

9. A process in accordance with claim 2 wherein the reacting of the at least one reactant olefinic organic compound is carried out for a time between about 0.1 second and about 10 hours.

10. A process in accordance with claim 2 wherein the electromagnetic radiation is ultraviolet radiation.

11. A process in accordance with claim 1 wherein the exposing of the solid catalyst to electromagnetic radiation is carried out in the presence of at least one olefinic organic compound prior to the reacting of the at least one reactant olefinic organic compound.

12. A process in accordance with claim 1 wherein the exposing of the solid catalyst to electromagnetic radiation is carried out in the presence of at least one olefinic organic compound during the reacting of the at least one olefinic organic compound.

13. A process in accordance with claim 12 wherein the exposing of the solid catalyst to electromagnetic radiation is carried out continuously during the reacting of the at least one olefinic organic compound.

14. A process in accordance with claim 12 wherein the exposing of the solid catalyst to electromagnetic radiation is carried out intermittently during the reacting of the at least one olefinic organic compound.

15. A process in accordance with claim 1 wherein the exposing of the solid catalyst to electromagnetic radiation is carried out both prior to and during the reacting of the at least one olefinic organic compound.

16. A process in accordance with claim 1 wherein the exposing of the solid catalyst to electromagnetic radiation is in the presence of at least one reactant olefinic organic compound.

17. A process in accordance with claim 1 wherein the exposing of the solid catalyst to electromagnetic radiation is in the presence of at least one olefinic organic compound other than a reactant olefinic organic compound.

18. A process in accordance with claim 17 wherein the exposing of the solid catalyst to electromagnetic radiation is in the presence of at least one olefinic organic compound selected from the group consisting of ethylene, propylene and butene.

19. A process in accordance with claim 1 wherein the transition metal of the solid catalyst is a metal selected from the group consisting of molybdenum and tungsten.

20. A process in accordance with claim 19 wherein the essentially inert solid support is silica.

21. A process in accordance with claim 1 wherein the compound selected from the group consisting of transition metal oxides, transition metal compounds convertible to oxides by calcination and mixtures thereof is present in the solid catalyst in an amount between about 0.1 and 30 percent by weight based on the total weight of said solid catalyst.

22. A process in accordance with claim 21 wherein the compound selected from the group consisting of transition metal oxides, transition metal compounds convertible to oxides by calcination and mixtures thereof is present in the solid catalyst in an amount between about 0.3 and 2.5 percent by weight based on the total weight of said solid catalyst.

23. A process in accordance with claim 1 wherein the olefinic organic compound is a mixture of at least one relatively high molecular weight olefinic organic compound and at least one relatively low molecular weight olefinic organic compound and the process comprises converting said high and low molecular weight olefinic organic compounds to at least one intermediate molecular weight olefinic organic compound.

24. A process for the redistribution of at least one olefinic bond of at least one reactant olefinic organic compound comprising contacting said at least one reactant olefinic organic compound with magnesium oxide, reacting the thus contacted at least one reactant olefinic organic compound with a catalyst active for said redistribution of at least one olefinic bond of at least one reactant olefinic organic compound, at a temperature, at a pressure and for a time sufficient to effect said redistribution of at least one olefinic bond of at least one reactant olefinic organic compound, at least one of said magnesium oxide and said catalyst being exposed to electromagnetic radiation having a wavelength of at least 1000 Å in the presence of at least one olefinic organic compound selected from the group consisting of at least one reactant olefinic organic compound, at least one olefinic organic compound other than a reactant olefinic organic compound and mixtures thereof, prior to said contacting and said reacting, during said contacting and said reacting or both prior to and during said contacting and said reacting.

25. A process in accordance with claim 24 wherein the magnesium oxide is thus exposed to electromagnetic radiation.

26. A process in accordance with claim 24 wherein the catalyst is thus exposed to electromagnetic radiation.

27. A process in accordance with claim 24 wherein both the magnesium oxide and the catalyst are thus exposed to electromagnetic radiation.

28. A process in accordance with claim 24 wherein the at least one of the magnesium oxide and the catalyst is thus exposed to electromagnetic radiation intermittently.

29. A process in accordance with claim 24 wherein the at least one magnesium oxide and catalyst is thus exposed to electromagnetic radiation continuously.

30. A process in accordance with claim 24 wherein the at least one of the magnesium oxide and the catalyst is thus exposed to electromagnetic radiation in the presence of at least one reactant olefinic organic compound.

31. A process in accordance with claim 24 wherein the at least one of the magnesium oxide and the catalyst is thus exposed to electromagnetic radiation in the presence of at least one olefinic organic compound other than a reactant olefinic organic compound.

32. A process in accordance with claim 31 wherein the at least one of the magnesium oxide and the catalyst is thus exposed to electromagnetic radiation in the presence of at least one olefinic organic compound selected from the group consisting of ethylene, propylene and butene.

33. A process in accordance with claim 24 wherein the at least one of the magnesium oxide and the catalyst is thus exposed to electromagnetic radiation prior to the contacting and the reacting.

34. A process in accordance with claim 24 wherein the at least one of the magnesium oxide and the catalyst is thus exposed to electromagnetic radiation during the contacting and the reacting.

35. A process in accordance with claim 24 wherein the at least one of the magnesium oxide and the catalyst is thus exposed to electromagnetic radiation both prior to and during the contacting and the reacting.

36. In a process for the isomerization of at least one reactant olefinic organic compound including reacting said at least one reactant olefinic organic compound with a catalyst active for the isomerization of said at least one reactant olefinic organic compound at a temperature, at a pressure and for a time sufficient to effect said isomerization of said at least one reactant olefinic organic compound, the improvement comprising; exposing said catalyst to electromagnetic radiation having a wavelength of at least about 1000 Å in the presence of at least one olefinic organic compound selected from the group consisting of at least one reactant olefinic organic compound, at least one olefinic organic compound other than a reactant olefinic organic compound, said exposing of said catalyst to electromagnetic radiation being carried out prior to said reacting of said at least one olefinic organic compound, during said reacting of said at least one reactant olefinic organic compound or both prior to and during said reacting of said at least one reactant olefinic organic compound.

37. A process in accordance with claim 36 wherein the exposing of the catalyst to electromagnetic radiation is carried out prior to the reacting of the at least one reactant olefinic organic compound.

38. A process in accordance with claim 36 wherein the exposing of the catalyst to electromagnetic radiation is carried out during the reacting of the at least one olefinic organic compound.

39. A process in accordance with claim 36 wherein the exposing of the catalyst to electromatic radiation is carried out both prior to and during the reacting of the at least one reactant olefinic organic compound.

40. A process in accordance with claim 36 wherein the exposing of the catalyst to electromagnetic radiation is in the presence of at least one reactant olefinic organic compound.

41. A process in accordance with claim 36 wherein the exposing of the catalyst to electromagnetic radiation is in the presence of at least one olefinic organic compound other than a reactant olefinic organic compound.

42. A process in accordance with claim 41 wherein the exposing of the catalyst to electromagnetic radiation is in the presence of at least one olefinic organic compound selected from the group consisting of ethylene, propylene and butene.

43. A process in accordance with claim 36 wherein the isomerization comprises the conversion of an olefinic organic compound having a terminal double bond to an olefinic organic compound having an internal double bond.

44. A process in accordance with claim 36 wherein the isomerization comprises the conversion of an olefinic organic compound having a cis configuration to an olefinic compound having a trans configuration.

45. A process in accordance with claim 36 wherein the temperature is between about −20° C. and 70° C.

* * * * *

UNITED STATES PATENT AND TRADEMARK OFFICE
CERTIFICATE OF CORRECTION

PATENT NO.  : 4,287,378
DATED       : September 1, 1981
INVENTOR(S) : Filippo Pennella It is certified that error appears in the above-identified patent and that said Letters Patent are hereby corrected as shown below:

Col. 17, Claim 24, line 61, change "1000 A" to 1000 $\overset{\circ}{A}$.

Signed and Sealed this

Twenty-fourth Day of November 1981

[SEAL]

Attest:

GERALD J. MOSSINGHOFF

Attesting Officer     Commissioner of Patents and Trademarks